(12) United States Patent
Okamura

(10) Patent No.: US 9,149,250 B2
(45) Date of Patent: Oct. 6, 2015

(54) ULTRASOUND DIAGNOSIS APPARATUS AND IMAGE-INFORMATION MANAGEMENT APPARATUS

(75) Inventor: Yoko Okamura, Nasushiobara (JP)

(73) Assignees: KABUSHIKI KAISHA TOSHIBA, Tokyo (JP); TOSHIBA MEDICAL SYSTEMS CORPORATION, Otawara-Shi (JP)

( * ) Notice: Subject to any disclaimer, the term of this patent is extended or adjusted under 35 U.S.C. 154(b) by 409 days.

(21) Appl. No.: 13/116,394

(22) Filed: May 26, 2011

(65) Prior Publication Data

US 2011/0295118 A1    Dec. 1, 2011

(30) Foreign Application Priority Data

Jun. 1, 2010    (JP) .................................. 2010-126057

(51) Int. Cl.
    *A61B 8/00*    (2006.01)
    *A61B 8/08*    (2006.01)
(52) U.S. Cl.
    CPC .............. *A61B 8/0825* (2013.01); *A61B 8/469* (2013.01)
(58) Field of Classification Search
    CPC ............................. A61B 8/0825; A61B 8/469
    USPC ........................................ 600/407, 437–472
    See application file for complete search history.

(56) References Cited

U.S. PATENT DOCUMENTS

2007/0239006 A1* 10/2007 Kamiyama et al. ........... 600/437
2009/0292206 A1   11/2009 Sato

FOREIGN PATENT DOCUMENTS

| CN | 100469316 C | 3/2009 |
| CN | 100469319 C | 3/2009 |
| CN | 101584589 A | 11/2009 |
| JP | 2001-327507 A | 11/2001 |
| JP | 2006-141466 A | 6/2006 |
| JP | 2010-172499 A | 8/2010 |

OTHER PUBLICATIONS

CN Office Action with English Summary for CN Application No. 201110151847.6 mailed on Jan. 21, 2013.

* cited by examiner

*Primary Examiner* — Mark Remaly
(74) *Attorney, Agent, or Firm* — Yoshida & Associates, LLC

(57) ABSTRACT

According to one embodiment, an ultrasound diagnosis apparatus includes an image memory, an output-information creating unit, and a control unit. The image memory associates and stores an ultrasound image and a first image that is set in accordance with a schematic image representing a portion imaged onto the ultrasound image and a positional image indicating a scanning position with ultrasound when creating the ultrasound image. The output-information creating unit creates a second image based on a shape of the first image stored by the image memory. The output-information creating unit then creates an image that image information extracted from the ultrasound image associated with the first image is superimposed onto the created second image, as output information. The control unit performs control of outputting the output information created by the output-information creating unit to an external device.

19 Claims, 10 Drawing Sheets

| MODE | IMAGE INFORMATION |
|---|---|
| MEASUREMENT MODE | MEASUREMENT RESULT |
| COLOR DOPPLER MODE | THERE IS BLOOD FLOW |
| CALCIFICATION-HIGHLIGHTED MODE | THERE IS CALCIFICATION |
| ⋮ | ⋮ |

ULTRASOUND DIAGNOSIS APPARATUS AND IMAGE-INFORMATION MANAGEMENT APPARATUS

CROSS-REFERENCE TO RELATED APPLICATIONS

This application is based upon and claims the benefit of priority from Japanese Patent Application No. 2010-126057, filed on Jun. 1, 2010; the entire contents of which are incorporated herein by reference.

FIELD

Embodiments described herein relate generally to an ultrasound diagnosis apparatus and an image-information management apparatus.

BACKGROUND

Conventionally, an ultrasound diagnosis apparatus plays an important role in today's medical care as a medical diagnostic imaging apparatus that has various advantages, such as simple operationality, noninvasiveness without risk of radiation exposure, and compactness of the apparatus scale.

Specifically, an ultrasound diagnosis apparatus can display a state of motion of an examination subject in real time, for example, beats of a heart or a motion of an embryo, by a simple operation of touching an ultrasound probe onto a body surface. Moreover, the ultrasound diagnosis apparatus has a high level of safety because of its noninvasiveness, thereby being able to perform examinations repeatedly. Furthermore, the ultrasound diagnosis apparatus is small in scale of apparatus, compared with other medical diagnostic imaging apparatuses, such as an X-ray diagnosis apparatus, an X-ray Computed Tomography (CT) apparatus, and a Magnetic Resonance Imaging (MRI) apparatus, so that an examination at a bed side by being moved there can be easily performed. Moreover, among ultrasound diagnosis apparatuses without risk of radiation exposure, an apparatus that is down-sized to be carried with one hand has been developed, such ultrasound diagnosis apparatus can be easily used in a medical practice, such as a maternity, or home care.

According to an examination using such ultrasound diagnosis apparatus, an ultrasound image rendered of a tissue directly under a touched ultrasound probe can be created and displayed in real time, so that a plurality of ultrasound images is recorded by moving the ultrasound probe on an examination target portion during the examination. When recording, to identify which portion of the subject is taken onto each ultrasound image, a "mark" indicating positional information is recorded onto the image. Particularly, in a case of examination of a mamma, because no organ or no blood vessel to be a landmark is included, the "mark" is noteworthy and required for recording an ultrasound image. Such "mark" can be a body mark representing an organ to be examined, or a mark indicating a scanning position with ultrasound in the organ.

When registering information about an ultrasound image recorded in this way (image information) onto a chart as a report, a reading doctor writes a position at which the ultrasound image is taken and a comment obtained from the ultrasound image, onto a schema on which an examination target portion can be recognized at a glance.

The reading doctor writes a comment on a lesion into the schema after the ultrasound examination is performed while reconfirming ultrasound images and data collected from the ultrasound images, thereby creating a report. The schema onto which a comment on a lesion is described is a schema manually rendered by the reading doctor, or a schema for a report that is registered in an electric chart system. Furthermore, a method of managing a report created by such processing has been also developed.

According to a conventional report preparation, after an examination with ultrasound is performed, all images need to be checked and then only required information needs to be reconfirmed and recorded, so that the operation requires a reading doctor to expend time and effort.

DETAILED DESCRIPTION

According to one embodiment, an ultrasound diagnosis apparatus includes an image storage unit, an output-information creating unit, and a control unit. The image storage unit associates and stores an ultrasound image, and a first image that is set in accordance with a schematic image representing a portion imaged onto the ultrasound image and a positional image indicating a scanning position with ultrasound when creating the ultrasound image. The output-information creating unit creates a second image based on a shape of the first image stored by the image storage unit, and creates as output information an image that image information extracted from an ultrasound image associated with the first image is superimposed on created second image. The control unit performs control of outputting the output information created by the output-information creating unit to a predetermined external device.

Exemplary embodiments of an ultrasound diagnosis apparatus will be explained below in detail with reference to the accompanying drawings.

Figure 1:
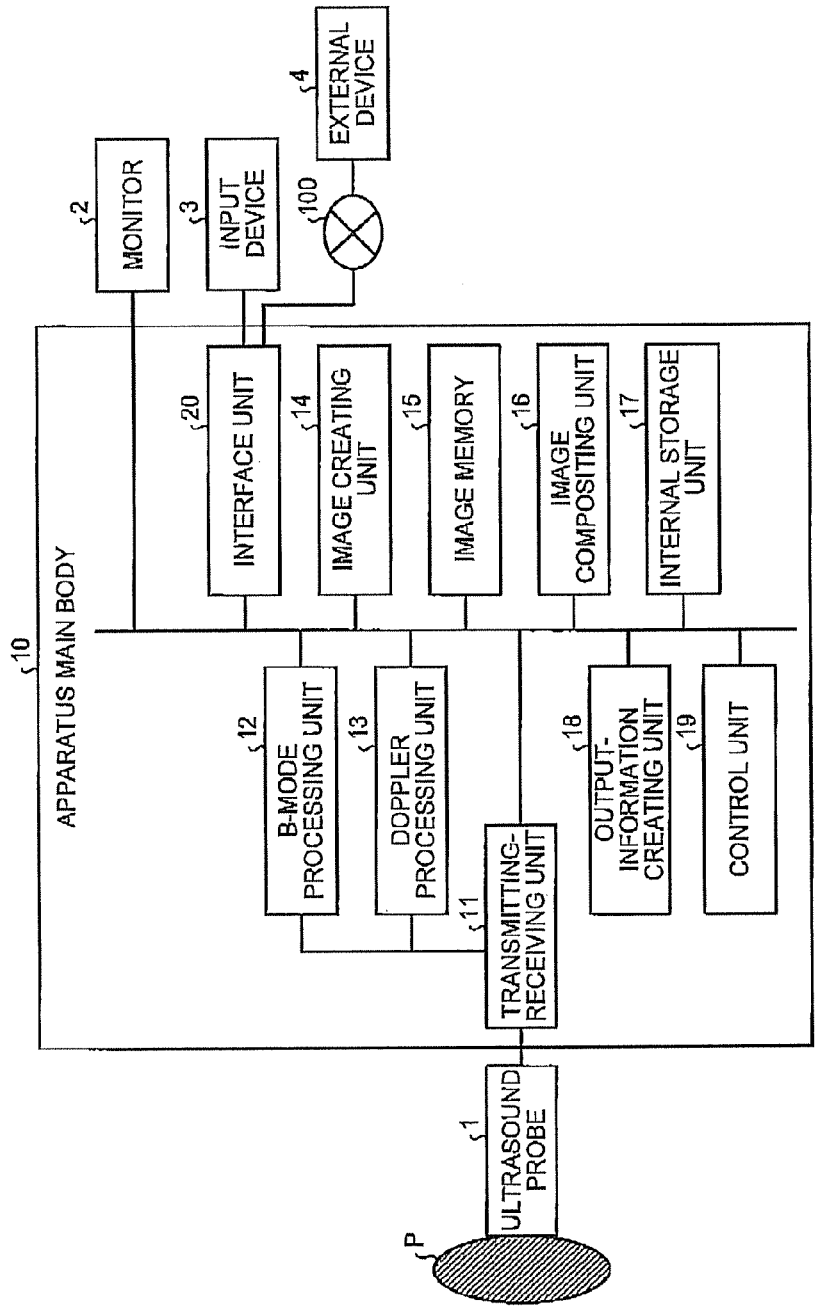
FIG. 1 is a schematic diagram for explaining a configuration of an ultrasound diagnosis apparatus according to a first embodiment.

First of all, a configuration of an ultrasound diagnosis apparatus according to a first embodiment is explained below. FIG. 1 is a schematic diagram for explaining the configuration of the ultrasound diagnosis apparatus according to the first embodiment. As shown in FIG. 1, the ultrasound diagnosis apparatus according to the first embodiment includes an ultrasound probe 1, a monitor 2, an input device 3, and an apparatus main body 10. Moreover, the apparatus main body 10 is connected to an external device 4 via a network 100.

The ultrasound probe 1 includes a plurality of piezoelectric vibrators; and the piezoelectric vibrators generate ultrasound based on a driving signal supplied from a transmitting-receiving unit 11 included in the apparatus main body 10 described later, and receive a reflected wave from a subject P and convert it into an electric signal. Moreover, the ultrasound probe 1 includes a matching layer provided to the piezoelectric vibrators, and a backing material that prevents propagation of ultrasound backward from the piezoelectric vibrators.

When ultrasound is transmitted from the ultrasound probe 1 to the subject P, the transmitted ultrasound is consecutively reflected by discontinuity planes of acoustic impedance in internal body tissue of the subject P, and received as a reflected wave signal by the piezoelectric vibrators included in the ultrasound probe 1. The amplitude of a received reflected wave signal depends on a difference in the acoustic impedance of the discontinuity planes that reflect ultrasound. A reflected wave signal when a transmitted ultrasound pulse is reflected by a moving blood flow or a surface of a heart wall is affected by a frequency deviation, dependently on a velocity component in the ultrasound transmitting direction of a moving object, due to the Doppler effect.

The input device 3 is to the apparatus main body 10 via an interface unit 20, which will be described later. The input device 3 includes a mouse, a keyboard, a button, a panel switch, a touch command screen, a foot switch, a trackball, and the like; receives various setting requests from an operator of the ultrasound diagnosis apparatus; and transfers each of the receives various setting requests to the apparatus main body 10. For example, the input device 3 receives an output request for output information, which will be described later.

The monitor 2 displays a Graphical User Interface (GUI) for the operator of the ultrasound diagnosis apparatus to input various setting requests by using the input device 3, and displays an ultrasound image created by the apparatus main body 10.

The external device 4 is a device that is connected to the apparatus lain body 10 via the interface unit 20, will be described later, for example, a printer, an electronic chart system, and an external storage device.

The apparatus main body 10 is a device that creates an ultrasound image based on a reflected wave received by the ultrasound probe 1; and includes the transmitting-receiving unit 11, a B-mode processing unit 12, a Doppler processing unit 13, an image creating unit 14, an image memory 15, an image compositing unit 16, an internal storage unit 17, an output-information creating unit 18, and a control unit 19, as shown in FIG. 1.

The transmitting-receiving unit 11 includes a trigger generating-circuit, a delay circuit, a pulsar circuit, and the like; and supplies a driving signal to the ultrasound probe 1. The pulsar circuit repeatedly generates a rate pulse for forming transmission ultrasound at a certain rate frequency. The delay circuit gives to each rate pulse generated by the pulsar circuit, a delay time with respect to each of the piezoelectric vibrators to be required for converging ultrasound generated from the ultrasound probe 1 into a beam and determining transmission directivity. The trigger generating circuit applies a driving signal (driving pulse) to the ultrasound probe 1 at timing based on the rate pulse. In other words, the delay circuit arbitrarily adjusts the transmitting direction from the piezoelectric vibrator plane by changing the delay time to be given to each rate pulse.

The transmitting-receiving unit 11 has a function of instantly changing the transmission frequency, the transmission driving voltage, and the like, to execute a certain scan sequence based on an instruction by the control unit 19, which will be described later. Particularly, a change of the transmission driving voltage is implemented by a transmission circuit of liner amplifier type that can instantly switch the value of the transmission driving voltage, or a mechanism of electrically switching a plurality of power supply units.

Moreover, the transmitting-receiving unit 11 includes an amplifier circuit, analog/digital (A/D) converter, an adder, and the like; and performs various kinds of processing on a reflected wave signal received by the ultrasound probe 1, thereby creating reflected wave data. The amplifier circuit performs gain correction processing by amplifying the reflected wave signal channel by channel. The A/D converter converts the reflected wave signal of which gain is corrected from analog-to-digital, and gives a delay time required for determining reception directivity to the digital data. The adder creates reflected wave data by performing addition processing of the reflected wave signal processed by the A/D converter. Through the addition processing by the adder, a reflection component from a direction in accordance with the reception directivity of the reflected wave signal is emphasized.

In this way, the transmitting-receiving unit 11 controls transmission directivity and reception directivity in transmission and reception of ultrasound.

The B-mode processing unit 12 receives from the transmitting-receiving unit-11 reflected wave data that is a processed reflected wave on which the gain correction processing, the A/D conversion processing, and the addition processing are performed; performs logarithmic amplification, envelope detection processing, and the like; and creates data (B-Mode data) that a signal strength is expressed by the brightness.

The Doppler processing unit 13 performs frequency analysis on velocity information from the reflected wave data received from the transmitting-receiving unit 11; extracts components of a blood flow, tissue, and contrast media echo by Doppler effects; and creates data (Doppler data) that moving object information, such as an average velocity, a distribution, a power, and the like, are extracted with respect to multiple points.

The image creating unit 14 creates a B-mode image on which the strength of a reflected wave is expressed in brightness from the B-mode data created by the B-mode processing unit 12. Moreover, the image creating unit 14 creates as an ultrasound image, a color Doppler image as an average velocity image, a distribution image, a power image, or a combination image of them, each of which indicates moving body information, from the Doppler data created by the Doppler processing unit 13.

Furthermore, the image creating unit 14 can create an image (for example, a calcification-highlighted image) on which a special target (for example, a calcified portion) is displayed in a highlighted manner by performing filtering processing-on B-mode data created by the B-mode processing unit 12.

In this way, the image creating unit 14 scans the same cross section of the subject P with ultrasound through different sequences, thereby creating ultrasound images in various modes in real time, such as a B-mode image, a color Doppler image, an image in a calcification-highlighted display mode, in accordance with the types of examination.

The image creating unit 14 converts (scan-converts) a scanning-line signal sequence of an ultrasound scan into a scanning-line signal sequence in a video format typified by television, and creates an ultrasound-image as a display image.

The image compositing unit 16 creates a composite image that text information about various parameters, a scale, a body mark, and the like, are composited onto an ultrasound image created by the image creating unit 14, and then outputs it to the monitor 2 as a video signal.

The image memory 15 is a memory that stores an ultrasound image created by the image creating unit 14, and a composite image created by the image compositing unit 16. The image creating unit 14 and the image compositing unit 16 associate the created ultrasound image and the created composite image with the subject P, respectively, and store them into the image memory 15.

The internal storage unit 17 stores control programs for performing ultrasound transmission and reception, image processing, and display processing, diagnosis information (for example, a patient ID, and a doctor's comment), and various data, such as a diagnosis protocol and various kinds of body marks. The control programs stored by the internal storage unit 17 include a measuring program for measuring the size of a certain portion (for example, a tumor) specified in an ultrasound image by the operator. A body mark is an image (schematic image) that schematically represents an organ or a portion imaged onto an ultrasound image. Moreover, a body mark is also called a pictogram.

Moreover, the internal storage unit 17 is used for storing images stored by the image memory 15, as required. Data stored by the internal storage unit 17 can be transferred to an external peripheral device (the external device 4) via the interface unit 20, which will be described later.

The output-information creating unit 18 creates output information described later from a composite image stored by the image memory 15. The output-information creating unit 18 will be described later in detail.

The control unit 19 controls the whole of processing performed by the ultrasound diagnosis apparatus. Specifically, the control unit 19 controls processing performed by the transmitting-receiving unit 11, the B-mode processing unit 12, the Doppler processing unit 13, the image creating unit 14, and the image compositing unit 16; and performs control of displaying an ultrasound image or a composite image stored by the image memory 15 onto the monitor 2; based on the various setting requests input by the operator via the input device 3 and the various control programs and the various data read from the internal storage unit 17. Moreover, the control unit 19 measures various index values indicating the size of a certain portion specified in an ultrasound image by the operator, based on the measuring program read from the internal storage unit 17.

Figure 2:
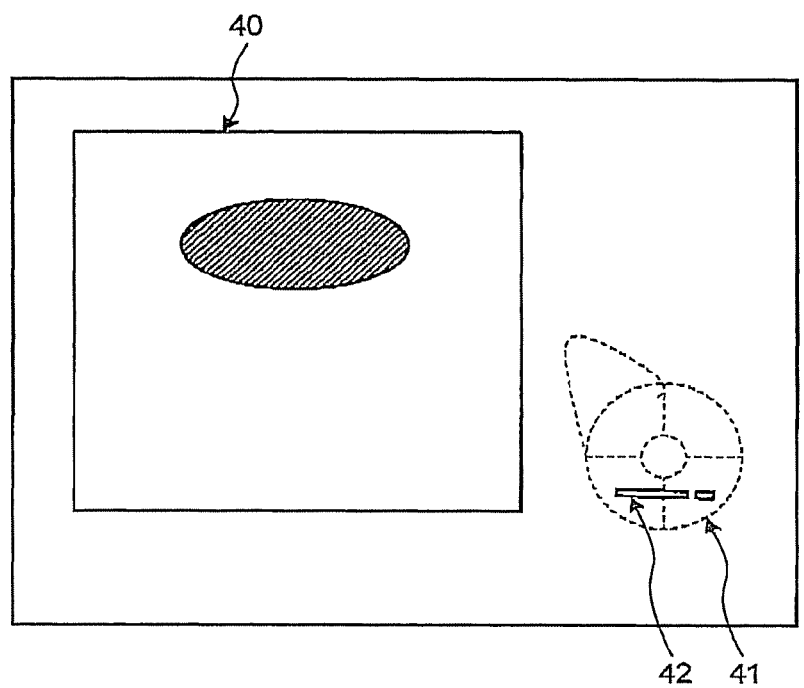
FIG. 2 is a schematic diagram for explaining a first image.

As described above, an overall configuration of the ultrasound diagnosis apparatus according to the first embodiment is explained. Under such configuration, the image creating unit 14 creates an ultrasound image through an examination among various types (modes), and the control unit 19 causes the monitor 2 to display the created ultrasound image. By referring to the ultrasound image displayed on the monitor 2, the operator then sets a schematic image (body mark) that schematically represents an organ or a portion imaged onto the ultrasound image, and a positional image indicating a scanning position with ultrasound when creating the ultrasound image. Hereinafter, an image that is set in accordance with a schematic image and a positional image is referred to as a "first image". FIG. 2 is a schematic diagram for explaining a first image.

For example, as shown in FIG. 2, the operator refers to B-mode image 40 that a right mamma of the subject P is imaged, sets a body mark 41 that is a schematic image schematically representing the right mamma by reading it from the internal storage unit 17, via the input device 3. Furthermore, the operator sets in the body mark 41 a positional image 42 indicating a scanning position with ultrasound when creating the ultrasound image, based on a position touched with the ultrasound probe 1 on the right mamma the subject P.

According to such settings, the image compositing unit 16 creates a composite image into which the B-mode image 40 and "a first image including the body mark 41 and the positional image 42" are combined, as shown in FIG. 2. The image compositing unit 16 then stores the created composite image into the image memory 15 when a storing request is received from the operator. The setting processing of a first image described above is similarly executed on an ultrasound image created through an examination in another mode, as well as a B-mode image. Specifically, the setting processing of a first image is performed on a color Doppler image created in a color Doppler mode, a calcification-highlighted image treated in a calcification-highlighted mode, or the like.

Accordingly, the image memory 15 stores an ultrasound image, and "a first image that is set with a schematic image representing a portion imaged onto the ultrasound image and a positional image indicating a scanning position with ultrasound when creating the ultrasound image", in an associated manner. Resulting from storing the first image, the image memory 15 is brought also storing information about a relative position of the positional image in the schematic image. Moreover, the image memory 15 stores the mode of the ultrasound image by associating it with the ultrasound image.

Figure 3:
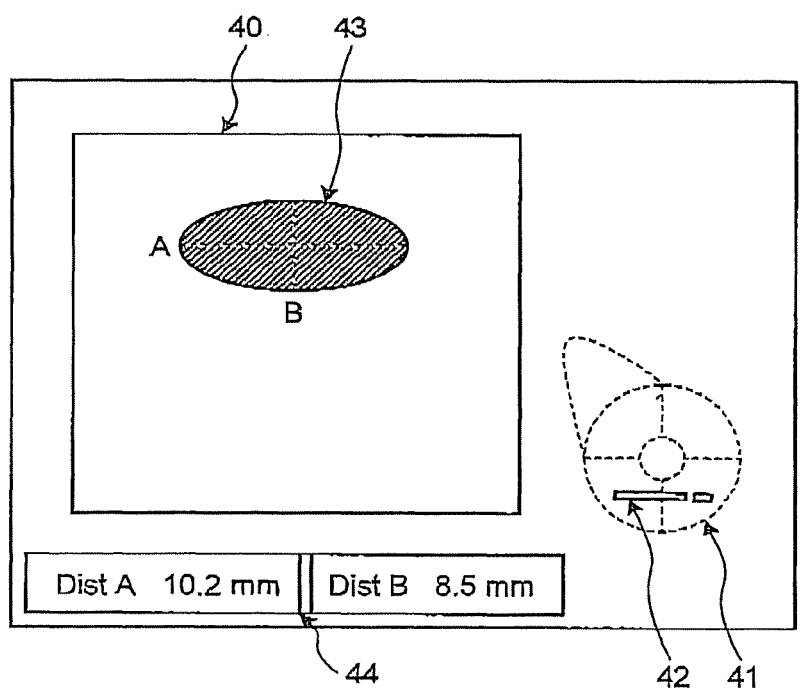
FIG. 3 is a schematic diagram for explaining measuring processing by using ultrasound image.

The operator who refers to the ultrasound image sometimes performs measuring processing on the ultrasound image in some cases. FIG. 3 is a schematic diagram for explaining the measuring processing by using ultrasound image.

For example, the operator measures a measurement target portion 43 on the B-mode image 40, as depicted in FIG. 3, by using the input device 3. In accordance with a measurement result, for example, as shown in FIG. 3, the control unit 19 causes display of "A: 10.2 millimeters, and B: 8.5 millimeters" as a-measurement result 44. According to an example shown in FIG. 3, a result of an ellipse measurement is displayed.

As well as causing display of the measurement result 44, the control unit 19 stores the measurement result 44 into the image memory 15 by also associating it with the B-mode image 40 and the first image including the body mark 41 and the positional image 42.

"An ultrasound image and a first image" or "an ultrasound image, a first image, and a measurement result" that are stored in accordance with a storing request by the operator are conventionally used when preparing a report of an examination using ultrasound image. According to the first embodiment, a report of an examination using ultrasound image can be easily prepared through processing by the output-information creating unit 18, which is explained below.

Specifically, the output-information creating unit 18 creates a second image based on the shape of a first image stored by the image memory 15. More specifically, the output-information creating unit 18 sets an image that reflects image information extracted from an ultrasound image associated with a first image, into an image in the same shape as the shape of a schematic image (body mark), in accordance with relative positional relation of a positional image in the schematic image, thereby creating a second image. The output-information creating unit 18 then creates an image that image information extracted from the ultrasound image associated with the first image is superimposed onto the created second image, as output information. For example, after an examination of the same subject (the subject P) is performed, when the operator inputs an output request for output information about the ultrasound examination of the subject P via the input device 3 together with an identification (ID) of the subject P and an examination ID, the processing by the output-information creating unit 18 is executed.

Figures 4, 5:
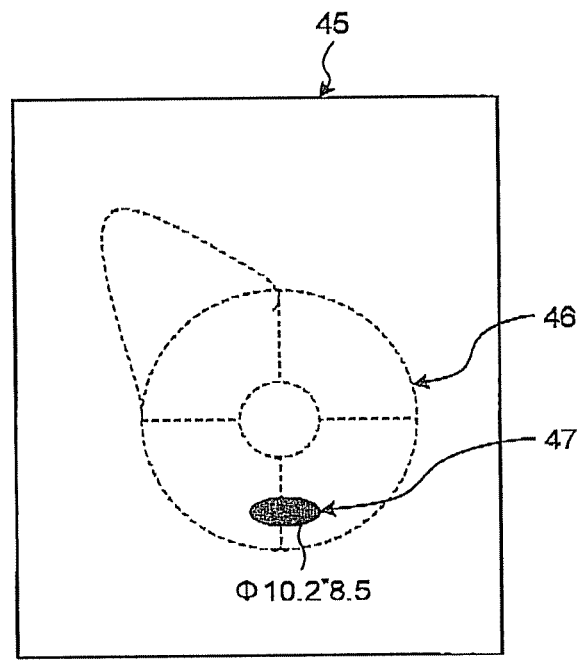
FIG. 4 is a schematic diagram for explaining an example of association information.
FIG. 5 is a schematic diagram for explaining an output image in a measurement mode.

The internal storage unit 17 stores association information that a type of image information to be superimposed on a second image is associated with each mode of examination using ultrasound, and the output-information creating unit 18 sets image information to be superimposed onto a second image by referring to the association information. FIG. 4 is a schematic diagram for explaining an example of association information.

For example, as shown in FIG. 4, the internal storage unit 17 stores association information that "mode: measurement mode" is associated with "image information: measurement result". In other words, the internal storage unit 17 stores association information that a measurement result is to be described in output information as image information, with respect to an ultrasound image associated with measurement result in accordance with the measurement mode. Moreover, for example, as shown in FIG. 4, the internal storage unit 17 stores association information that "mode: color-Doppler mode" is associated with "image information: there is a blood flow". In other words, the internal storage unit 17 stores association information that a comment of "there is a blood flow" is to be described in output information as image information, with respect to a color Doppler image. Furthermore, for example, as shown in FIG. 4, the internal storage unit 17 stores association information that "mode: calcification-highlighted mode" is associated with "image information: there is calcification". In other words, the internal storage unit 17 stores association information that a comment of "there is calcification" is to be described in output information as image information, with respect to calcification-highlighted image.

Figure 6:
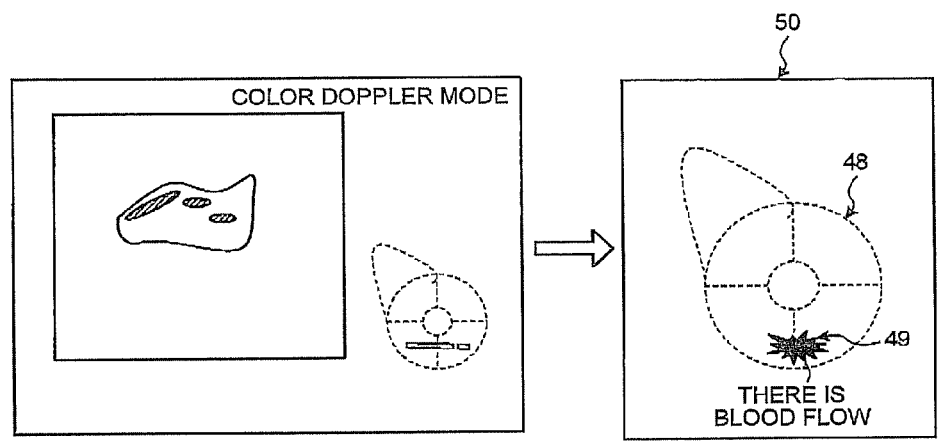
FIG. 6 is a schematic diagram for explaining an output image in a color Doppler mode.

Based on such association-information, a concrete example of output information created by the output-information creating unit 18 is explained below with reference to FIGS. 5 to 7. FIG. 5 is a schematic diagram for explaining an output image in the measurement mode; FIG. 6 is a schematic diagram for explaining an output image in the color Doppler mode; and FIG. 7 is a schematic diagram for explaining an output image in the calcification-highlighted mode.

For example, when creating output information from a composite image in the measurement mode shown in FIG. 3, the output-information creating unit 18 creates an image 46 formed in the same shape as the shape of the body mark 41 (see FIG. 5). As shown in FIG. 5, the output-information creating unit 18 then sets an image 47 that schematically represents the measurement target portion 43 in the image 46, in accordance with relative positional relation of the positional image 42 in the body mark 41. In other words, the output-information creating unit 18 creates a second image of the image 46 and the image 47 based on the shapes of the body mark 41 and the positional image 42 in the first image. The output-information treating unit 18 then superimposes "ϕ10.2×8.5" expressing the content of the measurement result 44 as the image information onto the vicinity of the image 47 in the second image as shown in FIG. 5, by referring to the above association information, thereby creating output information 45.

Moreover, when creating output information from a composite image in the color Doppler mode shown in the left figure in FIG. 6, the output-information creating unit 18 creates an image 48 formed in the same shape as the shape of the body mark (see the right figure in FIG. 6). As shown in the right figure in FIG. 6, the output-information creating unit 18 then sets an image 49 that schematically represents that there is a blood flow in the image 48, in accordance with relative positional relation of the positional image in the body mark. As shown in the right figure in FIG. 6, the output-information creating unit 18 then superimposes the comment "there is a blood flow" as the image information onto the vicinity of the image 49 in the second image by referring to the above association information, thereby creating output information 50.

Figure 7:
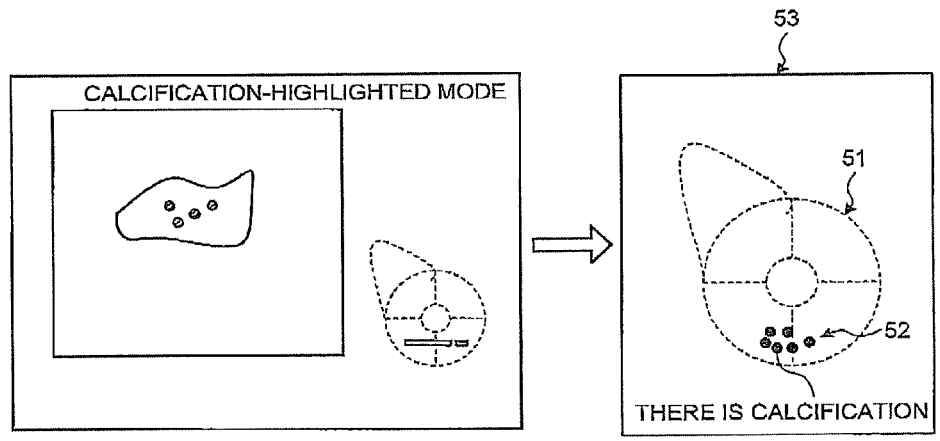
FIG. 7 is a schematic diagram for explaining an output image in a calcification-highlighted mode.

Furthermore, when creating output information from a composite image in the calcification-highlighted mode shown in the left figure in FIG. 7, the output-information creating unit 18 creates an image 51 formed in the same shape as the shape of the body mark (see the right figure in FIG. 7). As shown in the right figure in FIG. 7, the output-information creating unit 18 then sets an image 52 that schematically represents that there is calcification in the image 51, in accordance with relative positional relation of the positional image in the body mark. As shown in the right figure in FIG. 7, the output-information creating unit 18 then superimposes the comment "there is a calcification" as the image information onto the vicinity of the image 52 in the second image by referring to the above association information, thereby creating output information 53.

Among ultrasound examinations, a plurality of ultrasound images is sometimes stored with respect to the same tissue of the same subject (the subject P), and a report needs to be prepared from the plurality of ultrasound images, in some cases.

When the image memory 15 stores a plurality of ultrasound images associated with a first image including the same schematic image (body mark) among a plurality of ultrasound images taken from the same subject, the output-information creating unit 18 according to the first embodiment creates a second image by superimposing images based on respective positional images of the ultrasound images onto the same schematic image, and further superimposes image information about the respective ultrasound images onto the vicinities of the images based on the corresponding positional images. Accordingly, the output-information creating unit 18 according to the first embodiment creates an output image.

Figure 8:
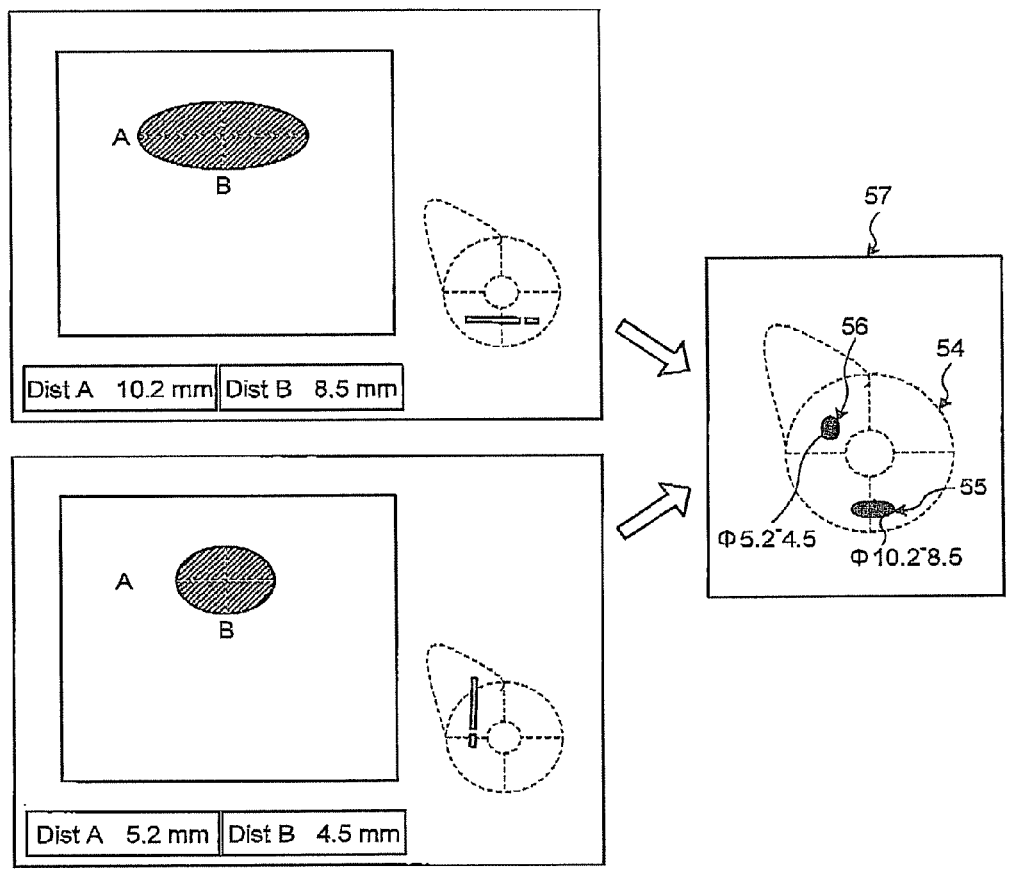
FIG. 8 is a schematic diagram for explaining output information created from a plurality of ultrasound images.

A case of creating output information from a plurality of ultrasound images is explained below with reference to FIG. 8. FIG. 8 is a schematic diagram for explaining output information created from a plurality of ultrasound images.

The left figures in FIG. 8 depict composite images that respective two B-mode images taken of the right mamma of the subject P at two different ultrasound scanning positions are each combined with a body mark, a positional image, and a measurement result. In other words, the two composite images in the measurement mode shown in the left figures in FIG. 8 are set with respective positional images at the different positions in the same body mark. Moreover, the two composite images in the measurement mode shown in the left figures in FIG. 8 are provided with descriptions of respective measurement results of the measurement target portions set in the composite images. Precisely, the composite image shown in the upper left figure in FIG. 8 is provided with a description of a measurement result "A: 10.2 millimeters, and B: 8.5 millimeters"; and the composite image shown in the lower left figure in FIG. 8 is provided with a description of a measurement result "A: 5.2 millimeters, and B: 4.5 millimeters".

In such case, the output-information creating unit 18 creates an image 54 formed in the same shape as the shape of the body mark, as shown in the right figure in FIG. 8. The output-information creating unit 18 then sets an image 55 and an image 56 that schematically represent two measurement target portions in the image 54, as shown in the right figure in FIG. 8, in accordance with relative positional relation of the respective positional images of the two composite images with respect to the body mark. Accordingly, the output-information creating unit 18 creates a second image that includes the images 54, 55, and 56. The output-information creating unit 18 then superimposes a measurement result "φ10.2×8.5" of the composite image shown in the upper left figure in FIG. 8 onto the vicinity of the image 55 in the second image as shown in the right figure in FIG. 8, by referring to the above association information. Moreover, the output-information creating unit 18 superimposes a measurement result "φ5.2×4.5" of the composite image shown in the lower left figure in FIG. 8 onto the vicinity of the image 56 in the second image as shown in the right figure in FIG. 8, by referring to the above association information. Accordingly, the output-information creating unit 18 creates one piece of output information 57 from the plurality of ultrasound images taken from the same tissue of the subject P.

The example shown it FIG. 8 is explained above in the case of creating output information from a plurality of images in the measurement mode taken from the same subject. However, the first embodiment can be in a case of creating output information from a plurality of images, for example, in the color Doppler mode or the calcification-highlighted mode. Moreover, the first embodiment can be in a case of creating output information from images in different modes taken from the same subject.

The control unit 19 shown in FIG. 1 performs control so as to output the output information created by the output-information creating unit 18 to the external device 4 via the interface unit 20 and the network 100 based on an output request by the operator. For example, the control unit 19 performs control such that output information is to be printed by a printer that is the external device 4. As another example, the control unit 19 performs control so as to transfer output information as a chart of the subject P to an electronic chart system that is the external device 4. The control unit 19 shown in FIG. 1 can also perform control so as to display output information on the monitor 2, and control so as to store it into the internal storage unit 17.

Figure 9:
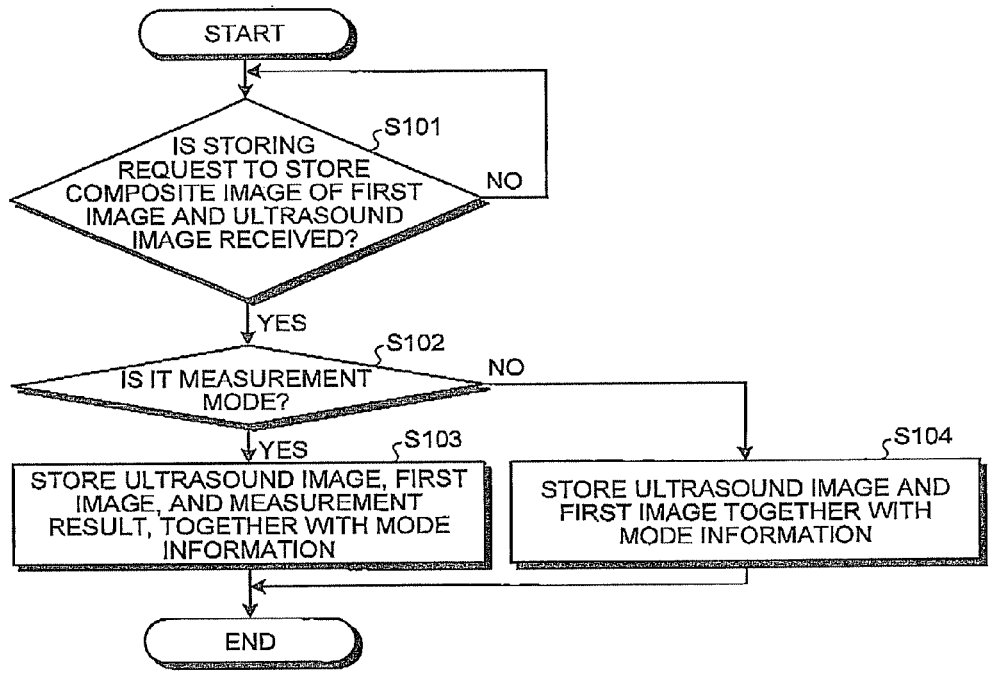
FIG. 9 is a schematic diagram for explaining image storing processing performed by the ultrasound diagnosis apparatus according to the first embodiment.
Figure 10:
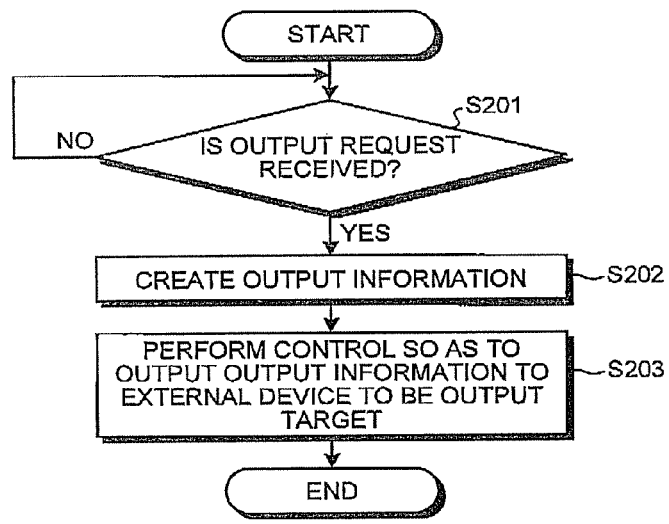
FIG. 10 is a schematic diagram for explaining output-information creating processing performed by the ultrasound diagnosis apparatus according to the first embodiment.

Processing performed by the ultrasound diagnosis apparatus according to the first embodiment is explained below with reference to FIGS. 9 and 10. FIG. 9 is a schematic diagram for explaining image storing processing performed by the ultrasound diagnosis apparatus according to the first embodiment; and FIG. 10 is a schematic diagram for explaining output-information creating processing performed by the ultrasound diagnosis apparatus according to the first embodiment.

As shown in FIG. 9, the ultrasound diagnosis apparatus according to the first embodiment determines whether a storing request to store the composite image of the ultrasound image and the first image that is set from the schematic image (body mark) and the ultrasound scanning direction is received (Step S101). If the storing request is not received (No at Step S101), the ultrasound diagnosis apparatus turns on standby. By contrast, if the storing request is received (Yes at Step S101); the control unit 19 determines whether the composite image for which storing request is received is in the measurement mode that includes a measurement result (Step S102).

If it is in the measurement mode (Yes at Step S102); in accordance with an instruction by the control unit 19, the image compositing unit 16 associates the ultrasound image, the first image, and the measurement result with mode information, and stores them into the image memory 15 (Step S103), then terminates the processing.

By contrast, if it is not in the measurement mode (No at Step S102); in accordance with an instruction by the control unit 19, the image compositing unit 16 associates the ultrasound image and the first image with mode information, and stores them into the image memory 15 (Step S104), then terminates the processing. Resulting from storing the first image, the image memory 15 is brought also storing information about a relative position of the positional image in the schematic image.

As shown in FIG. 10, the ultrasound diagnosis apparatus according to the first embodiment then determines whether an output request for output information according to the ultrasound examination of the subject P is received (Step S201). If the output request is not received (No at Step S201), the ultrasound diagnosis apparatus turns on standby.

By contrast, if the output request is received (Yes at Step S201); the output-information creating unit 18 creates a second image based on a shape of the first image stored by the image memory 15, and creates output information that is an image that image information set from mode information and association information about an ultrasound image associated with the first image is superimposed onto the created second image (Step S202, see FIGS. 5 to 8).

The control unit 19 then performs control so as to output the output information to the external device 4 that is to be an output target (Step S203), and then terminates the processing.

As described above, according to the first embodiment, the image memory 15 stores an ultrasound image, ad a first image that is set with a schematic image representing a portion imaged onto the ultrasound image and a positional image indicating a scanning position with ultrasound when creating the ultrasound image, in an associated manner. The output-information creating unit 18 then creates a second image based on a shape of the first image stored by the image memory 15. The output-information creating unit 18 then creates as output information an image that image information extracted from the ultrasound image associated with the first image is superimposed onto the created second image. The control unit 19 then performs control so as to output the output information created by the output-information creating unit 18 to the external device 4 via the interface unit 20 and the network 100, based on an output request by the operator.

Precisely, according to the first embodiment, a report preparation that is conventionally performed while watching an ultrasound image again by filling image information into a manually-drawn schema, or a schema registered, for example, in an electronic chart system, can be automatically performed. In other words, the ultrasound diagnosis apparatus according to the first embodiment automatically produces a schema from a composite image of an ultrasound image, a living-body schematic image and a positional-information image; and furthermore, automatically superimposes image information onto the automatically produced schema, thereby automatically performing a report preparation. Therefore, according to the first embodiment, a report of an examination using ultrasound image can be easily prepared.

Moreover, according to the first embodiment the output-information creating unit 18 sets an image that reflects image information extracted from an ultrasound image associated with a first image, into an image in the same shape as the shape of a schematic image, in accordance with relative positional relation of a positional image in the schematic image, thereby creating a second image. Therefore, according to the first embodiment, a second image precisely reflecting information that is input when taking an ultrasound image can be automatically created, so that a report of an examination using ultrasound image can be more easily prepared.

Furthermore, according to the first embodiment, a body mark that schematically represents a portion or an organ imaged onto an ultrasound image is used as a schematic image. Therefore, according to the first embodiment, output information can be created by using a body mark that is conventionally registered in the ultrasound diagnosis apparatus, so that a report of an examination using ultrasound image can be far more easily prepared.

Moreover, according to the first embodiment, the internal storage unit 17 stores association information that a type of image information to be superimposed on a second image is associated with each mode of examination using ultrasound image, and the output-information creating unit 18 sets image information to be superimposed onto a second image by referring to the association information. Therefore, according to the first embodiment, output information that image information in accordance with the examination mode is automatically transcribed onto a second image can be created.

Furthermore, according to the first embodiment, when the image memory 15 stores a plurality of ultrasound images associated with a first image including the same schematic image (body mark) among a plurality of ultrasound images taken from the same subject, the output-information creating unit 18 creates a second image by superimposing images based on respective positional images of the ultrasound images onto the same schematic image, and further superimposes image information about the respective ultrasound images onto the vicinities of the images based on the corresponding positional images, thereby creating an output image.

Therefore, according to the first embodiment, even when there is a plurality of lesions in the same tissue of the same subject, time and effort for a reading doctor to prepare a report by watching again a plurality of ultrasound images of the same subject can be avoided.

The first embodiment is explained above in the case where the same ultrasound image includes one piece of image information. However, the same ultrasound image sometimes includes a plurality of pieces of image information in some cases among ultrasound examinations. For example, sometimes there is a case of performing measurements on a plurality of measurement target portions due to a plurality of tumors that is observed at different positions in an ultrasound image created at the same ultrasound scanning position.

Figure 11:
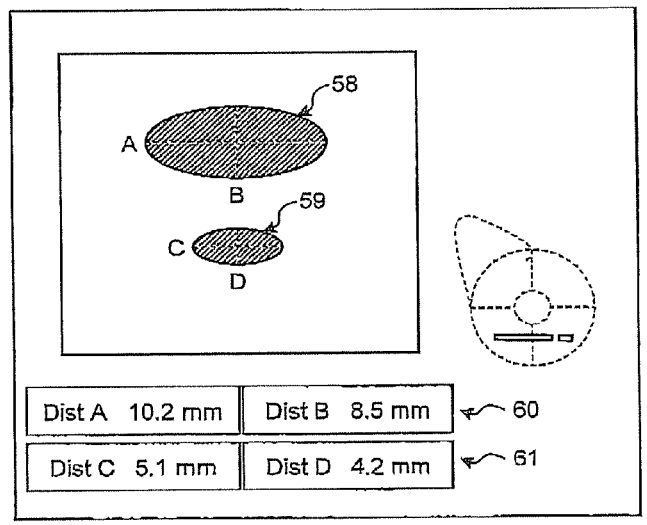
FIGS. 11, 12, and 13 are schematic diagrams for explaining and example that a plurality of output images is created from a same ultrasound image.
Figure 12:
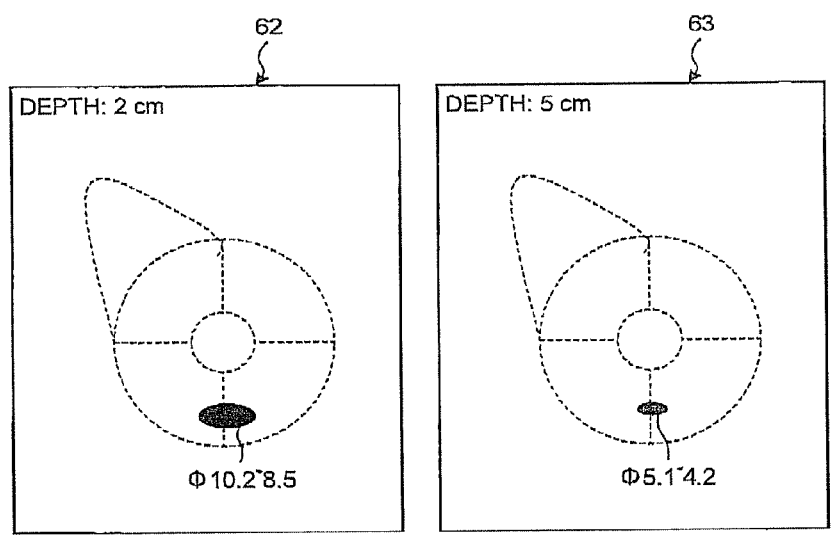
Figure 13:
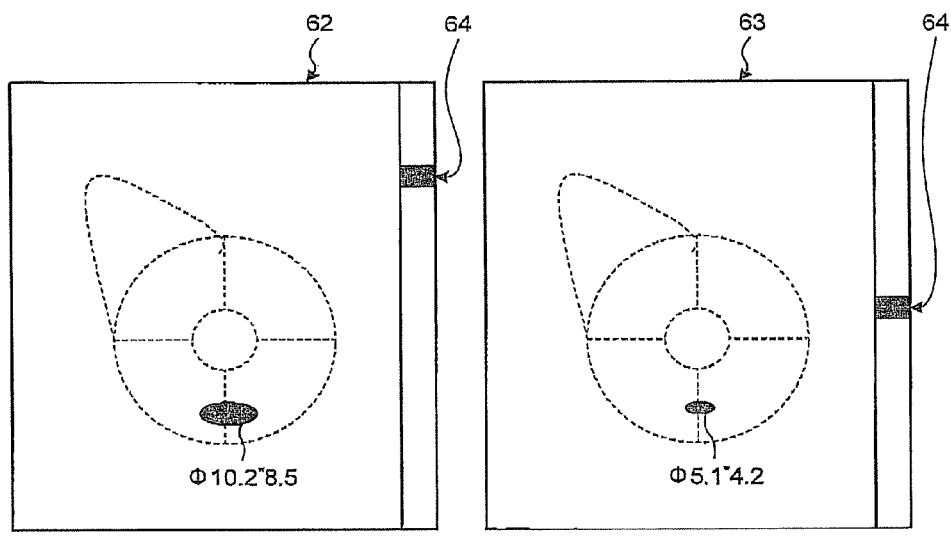

In such case, the output-information creating unit 18 creates a plurality of pieces of output information that a plurality of pieces of image information is superposed on second images, based on information about depths in the ultrasound image of the respective pieces of image information. FIGS. 11 to 13 are schematic diagrams for explaining an example of creating a plurality of output images from the same ultrasound image.

For example, FIG. 11 depicts a composite image that two measurement results are combined with a first image by setting two measurement target portions in different depths along the ultrasound transmitting direction on the same B-mode image. For example, FIG. 11 depicts that a measurement result 60 of a measurement target portion 58 at a position "two centimeters" from the ultrasound probe 1 is "A (longitudinal diameter): 10.2 millimeters, and B (transverse diameter): 8.5 millimeters", and a measurement result 61 of a measurement target portion 59 at a position "five centimeters" from the ultrasound probe 1 is "C (longitudinal diameter): 5.1 millimeters, and D (transverse diameter): 4.2 millimeters".

In such case, as shown in the left figure in FIG. 12, the output-information creating unit 18 creates a second image that an image schematically representing the measurement target portion 58 is set in an image formed in the same shape as the shape of the body mark shown in FIG. 11. The output-information creating unit 18 then superimposes "φ10.2×8.5" expressing the content of the measurement result 60 and depth information "two centimeters", thereby creating output information 62, as shown in the lower left figure in FIG. 12.

Moreover, as shown in the lower right figure in FIG. 12, the output-information creating unit 18 creates a second image that an image schematically representing the measurement target portion 59 is set in an image formed in the same shape as the shape of the body mark shown in FIG. 11. The output-information creating unit 18 then superimposes "φ5.1×4.2" expressing the content of the measurement result 61 and depth information "five centimeters", thereby creating output information 63, as shown in the lower right figure in FIG. 12.

Alternatively, to enable a person who refers to the output information to recognize three-dimensionally respective pieces of depth information about the measurement portions, the output-information creating unit 18 creates at first a plurality of images formed in the same shape as the shape of the body mark shown in FIG. 11, as a plurality of pieces of output information not including image information. The output-information creating unit 18 then inserts the output information 62 and 63 into the pieces of output information not including image information, based on the pieces of depth information. The output-information creating unit 18 then creates one piece of data, by bundling a plurality of output images created by such processing with a scroll bar 64, as shown in FIG. 13. The reading doctor can refers to the output information 62 and 63 at a position in accordance with the depth information, by moving the scroll bar 64 up or down, as shown in FIG. 13.

In this way, according to a modification of the first embodiment, when there is a plurality of pieces of image information in the same ultrasound image, the output-information creating unit 18 creates a plurality of pieces of output information that a plurality of pieces of image information is superposed on second images, based on information about depths in the ultrasound image of the respective pieces of image information. Therefore, according to the modification, even when there is a plurality of pieces of image information in the same ultrasound image, a report of an examination using ultrasound image can be easily prepared.

A second embodiment is explained below in a case where output information is creates only about a specified ultrasound image.

The output-information creating unit 18 according to the second embodiment creates output information only about an ultrasound image that is specified by the operator. For example, when storing a composite image, the operator specifies whether or not to use it for outputting output information.

Accordingly, the image compositing unit 16 associates it with a flag indicating that it is for output, together with an ultrasound image and a first image, and stores them into the image memory 15, for example. When an output request for output information according to an ultrasound examination of the subject P is received, the output-information creating unit 18 creates an output image only from an ultrasound image associated with the flag among a plurality of ultrasound images of the subject P.

Figure 14:
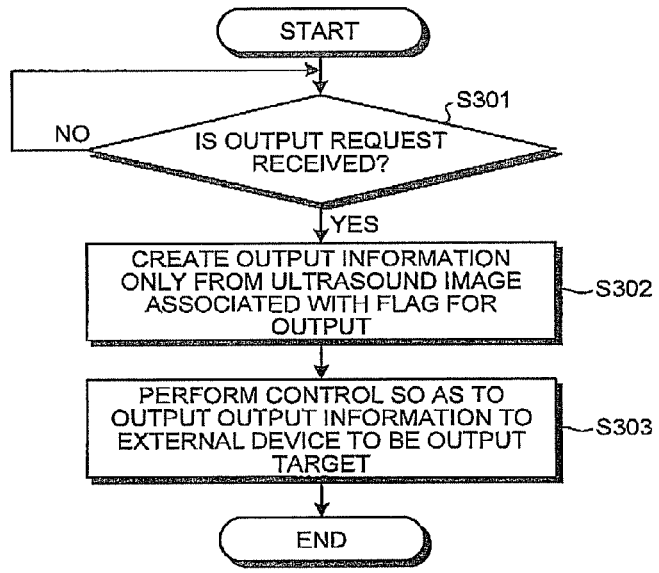
FIG. 14 is a schematic diagram for explaining output-information creating processing performed by an ultrasound diagnosis apparatus according to a second embodiment.

Processing performed by the ultrasound diagnosis apparatus according to the second embodiment is explained below with reference to FIG. 14. FIG. 14 is a schematic diagram for explaining output-information creating processing performed by the ultrasound diagnosis apparatus according to the second embodiment. Image storing processing by the ultrasound diagnosis apparatus according to the second embodiment is similar to the image storing processing explained with reference to FIG. 9, except that a flag is associated when the processing is of storing an image for output, therefore explanation is omitted.

As shown in FIG. 14, the ultrasound diagnosis apparatus according to the second embodiment determines whether an output request for output information in the ultrasound examination of the subject P is received (Step S301). If the output request is not received (No at Step S301), the ultrasound diagnosis apparatus turns on standby.

By contrast, if the output request is received (Yes at Step S301); the output-information creating unit 18 creates a second image based on a shape of the first image only from an ultrasound image associated with a flag for output, and creates output information that is an image that image information set from mode information and association information about an ultrasound image associated with the first image is superimposed onto the created second image (Step S302).

The control unit 19 then performs control so as to output the output information to the external device 4 that is to be an output target (Step S303), and then terminates the processing.

As described above, according to the second embodiment, the output-information creating unit 18 creates output information only with respect to an ultrasound image specified by the operator. Therefore, according to the second embodiment, output information can be created only from an ultrasound image determined by the reading doctor as it is useful for report preparation.

Figure 15:
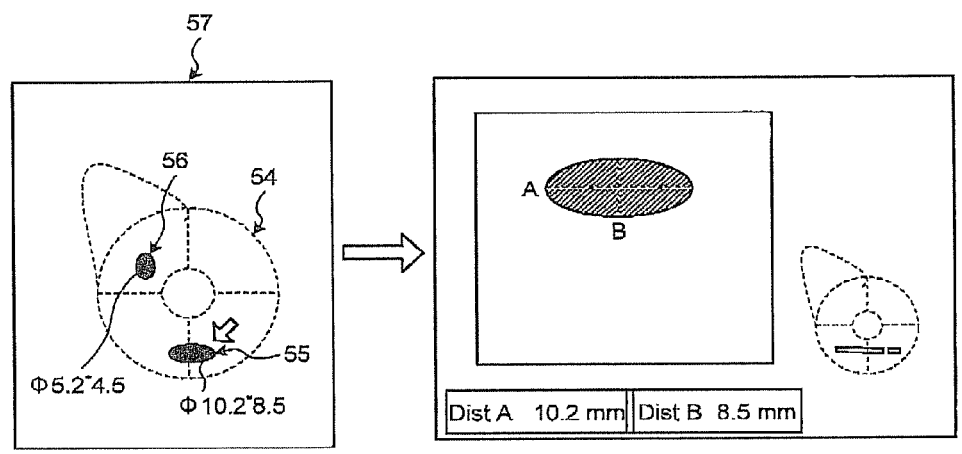
FIG. 15 is a schematic diagram for explaining a control unit according to a third embodiment.

According to a third embodiment, processing using output information is explained below with reference to FIG. 15. FIG. 15 is a schematic diagram for explaining a control unit according to the third embodiment.

The control unit 19 according to the third embodiment performs control when the operator who refers to output information specifies a piece of image information in the output information, so as to display an ultrasound image from which the specified piece of image information is extracted, onto the monitor 2.

Processing performed by the control unit 19 according to the third embodiment is explained below by using the output information 57 explained with reference to FIG. 8. For example, as shown in the left figure in FIG. 15, when the image 55 that schematically represents a measurement target portion of a measurement result "ϕ10.2×8.5" is specified by the reading doctor with the input device 3, such as a mouse, the control unit 19 reads from the image memory 15 a composite image of an ultrasound image (B-mode image) rendered of the measurement target portion from which the image 55 is created, based on relative positional information about the image 55 in the image 54. The control unit 19 then performs control so as to display the read composite image onto the monitor 2, as shown in the right figure in FIG. 15. The third embodiment can be in a case where there is one piece of image information in output information, as the operator specifies the one piece of image information, an ultrasound image or a composite image that is an extraction source of the image information is displayed.

Figure 16:
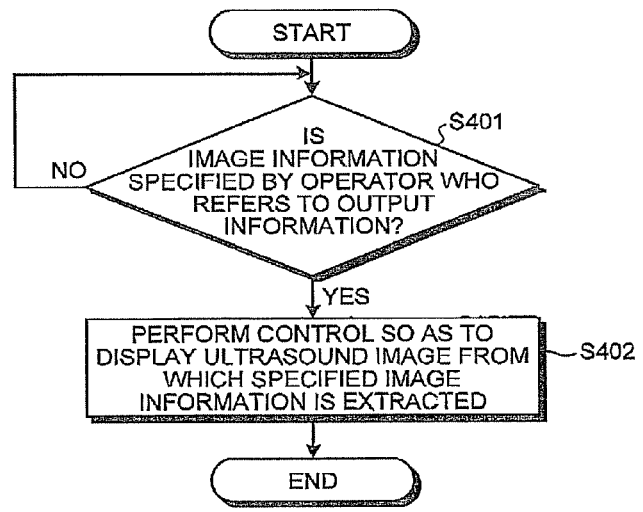
FIG. 16 is a schematic diagram for explaining processing performed an ultrasound diagnosis apparatus according to the third embodiment.

Processing performed by the ultrasound diagnosis apparatus according to the third embodiment is explained below with reference to FIG. 16. FIG. 16 is a schematic diagram for explaining processing performed by the ultrasound diagnosis apparatus according to the third embodiment.

As depicted in FIG. 16, the ultrasound diagnosis apparatus according to the third embodiment determines whether image information in the output information is specified by the operator who refers to the output information about the subject P (Step S401). If the image information is not specified (No at Step S401), the ultrasound diagnosis apparatus turns on standby.

By contrast, if the image information is specified (Yes at Step S401); the control unit 19 performs control so as to display onto the monitor 2 the ultrasound image from which the specified image information is extracted (Step S402), and then terminates the processing.

As described above, according to the third embodiment, when the operator who refers to the output information specifies image information in the output information, the control unit 19 performs control so as to display onto the monitor 2 the ultrasound image from which the specified image information is extracted. Conventionally, for example, in a case of a re-examination, a doctor needs to confirm a lesion part by seeing a comment in a report and finding an ultrasound image related to a comment considered as meaningful. However, according to the third embodiment, a doctor can refer to an ultrasound image related to a comment considered as meaningful, through a simple operation, such as specifying a piece of image information in output information. Therefore, according to the third embodiment, efficiency of an ultrasound examination can be improved.

Figure 17:
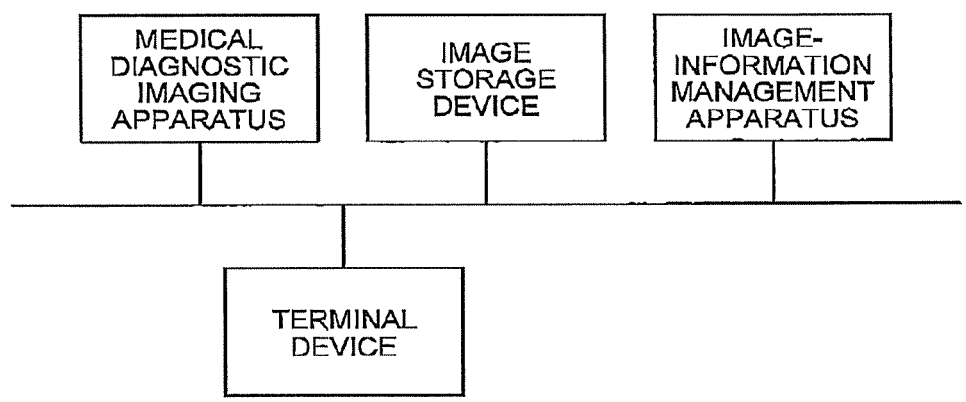
FIG. 17 is a schematic diagram for explaining a modification of the first to the third embodiment.

The first to the third embodiments are explained above in the cases where output-information creating processing and output control processing are executed in the ultrasound diagnosis apparatus. However, the output-information creating processing and the output control processing explained in the first to the third embodiments can be executed by an image-information management apparatus that is placed separately from the ultrasound diagnosis apparatus, by using ultrasound image created by the ultrasound diagnosis apparatus. Modifications using an image-information management apparatus placed separately from the ultrasound diagnosis apparatus are explained below. FIG. 17 is a schematic diagram for explaining a modification of the first to the third embodiment.

The image-information management apparatus is, for example, as shown in FIG. 17, placed as an apparatus included in an in-hospital system that is introduced in a hospital. As an in-hospital system, a Picture Archiving and Communication System (PACS), an electronic chart system, a Hospital Information System (HIS), a Radiology Information System (RIS), and the like, can be listed.

As shown in FIG. 17, a medical diagnostic imaging apparatus, an image storage device, and a terminal device are connected to such in-hospital system in conditions capable to communicate, for example, via a local area network (LAN) that is provided inside the hospital. The medical diagnostic imaging apparatus is an apparatus placed in the hospital, such as an ultrasound diagnosis apparatus, an X-ray diagnosis apparatus, an X-ray Computed Tomography (CT) apparatus, a Magnetic Resonance Imaging (MRI) apparatus, a Single Photon Emission Computed Tomography (SPECT) apparatus, a Positron Emission computed Tomography (PET) apparatus, a SPECT-CT apparatus that a SPECT apparatus and an X-ray CT apparatus are integrated, a PET-CT apparatus that a PET apparatus and an X-ray CT apparatus are integrated, or the like. The terminal device is a device that allows a doctor or an examination engineer who works in the hospital to view a medical image. For example, the terminal device is a personal computer (PC) that is operated by a doctor or an examination engineer who works in the hospital.

The image storage device is a device that receives data, such as a medical image taken by the medical diagnostic imaging apparatus, and supplemental information about the medial image, and stores and manages the received data. For example, the image storage device stores and manages "a composite image of an ultrasound image, a schematic image, and positional image" stored by the image memory 15, and "a measurement result of the composite image".

In other words, the image-information management apparatus can executes the processing explained in the first to the third embodiments by using data received by the image storage device from an ultrasound diagnosis apparatus, and can output a processing result to the terminal device. In such case, the image-information management apparatus can automatically perform report preparation, from each of ultrasound images taken by a plurality of ultrasound diagnosis apparatuses included in the in-hospital system, by cooperating with the image storage device. In other words, as the image-information management apparatus is installed in the in-hospital system, a report of an examination using ultrasound image can be easily prepared, similarly to the first to the third embodiments. The image-information management apparatus can be applied to a case where the image-information management apparatus is configured as an apparatus capable to store a massive volume of image data, so that the image-information management apparatus is integrated with the image storage device. Alternatively, it can be applied to a case where the image storage device is configured to function as the image-information management apparatus.

Furthermore, the image-information management apparatus described above can be applied to a case where the image-information management apparatus creates output information by using a medical image, such as an X-ray image, an X-ray CT image, an MRI image, a SPECT image, or a PET image, as well as an ultrasound image, as a medical image to be processed. In such case, the image storage device or the image-information management apparatus stores a medical image, and "a first image that is set with a schematic image representing a portion image onto the medical image and a positional image indicating the position of a region of interest in the medical image", in an associated manner.

For example, the image storage device or the image-information management apparatus stores an X-ray CT image of a chest. The image storage device or the image-information management apparatus then stores "a first image that is set with a schematic image schematically representing the chest and a positional image indicating the position of a Region Of Interest (ROI)", by associating it the X-ray CT image of the chest.

The image-information management apparatus then creates a second image based on the shape of the first image, and creates an image that image information extracted from a medical image associated with the first image is superimposed on the second image, as output information. For example, the image-information management apparatus creates an image that a measurement result of the region of interest in the X-ray CT image of the chest is superimposed onto the second image, as output information.

The image-information management apparatus then performs control so as to output the output information to a certain external device (for example, a terminal device). According to the modification, report preparation can be automatically performed from each of medical images taken by medial diagnostic imaging apparatuses included in an in-hospital system. In other words, as the image-information management apparatus is installed in the in-hospital system, a report of an examination using medical image can be easily prepared.

As explained above, according to the first to the third embodiments, a report of an examination using ultrasound image can be easily prepared.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasound diagnosis apparatus, comprising:
an input device configured to receive an user request for setting a positional image, indicating a scanning position regarding an ultrasound image, on a first schematic image schematically representing an imaged portion of the ultrasound image;
a memory configured to memorize position information indicating a position of the positional image on the first schematic image and the ultrasound image;
an output-information generator operationally connected to the memory and configured to generate an image information indicating a feature of the ultrasound image memorized in the memory, generate an image by superimposing the image information on a second schematic image having the substantially same shape as the first schematic image based upon the position information memorized in the memory, and output the image to a predetermined device as output information; and
a controller operationally connected to the output-information generator and configured to control an output of the output information to the predetermined device.

2. The ultrasound diagnosis apparatus according to claim 1, wherein the output-information generator generates the image as the output information by generating an image reflecting the image information and placing the generated image on an image portion within the second schematic image, the image portion being placed according to a relative position of the positional image within the first schematic image.

3. The ultrasound diagnosis apparatus according to claim 1, wherein the first schematic image is a body mark that references the imaged portion of the ultrasound image.

4. The ultrasound diagnosis apparatus according to claim 1, wherein the memory further memorizes association information that indicates a type of the image information to be superimposed onto the second schematic image for each of predetermined kinds of examinations using the ultrasound image; and the output-information generator selects a certain one of the image information to be superimposed onto the second schematic image based upon the association information.

5. The ultrasound diagnosis apparatus according to claim 1, wherein when the memory memorizes a plurality of the ultrasound images that have been taken from a same subject associated with a same one of the first schematic images, the output-information generator generates the image as the output information by superimposing images based on all of the positional images of the ultrasound images onto the second schematic image having the substantially same shape as the same first schematic image and further by superimposing each of the image information of the ultrasound images in vicinities of each of the images based on each of the positional images.

6. The ultrasound diagnosis apparatus according to claim 1, wherein when the output-information generator generates a plurality of the image information of a same one of the ultrasound image, the output-information generator generates a plurality of the images as a plurality of the output information by superimposing each of the image information on the second schematic image based on a corresponding depth of each of the plurality of the image information of the ultrasound image.

7. The ultrasound diagnosis apparatus according to claim 1, wherein the output-information generator generates the image as the output information only on a specified ultrasound image.

8. The ultrasound diagnosis apparatus according to claim 1, further comprising a display, wherein when an operator specifies a particular one of the image information in the output information after reviewing the output information, the controller controls the display of the ultrasound image from which the specified one of the extracted image information is generated onto the display.

9. The ultrasound diagnosis apparatus according to claim 1, wherein a type of the feature depends on an examination mode regarding to the ultrasound image.

10. The ultrasound diagnosis apparatus according to claim 1, wherein the first schematic image is the second schematic image.

11. An image information control apparatus, comprising:
a memory configured to memorize position information indicating a position of a positional image on a first schematic image and an ultrasound image, the first schematic image schematically representing an imaged portion of the ultrasound image, the positional image indicating a scanning position regarding the ultrasound image, the positional image being set on the first schematic image by an user;
an output-information generator operationally connected to the memory and configured to generate an image information indicating a feature of the ultrasound image memorized in the memory, generate an image by superimposing the image information on a second schematic image having the substantially same shape as the first schematic image based upon the position information memorized in the memory, and output the image to a predetermined device as output information; and
a controller operationally connected to the output-information generator and configured to control an output of the output information to the predetermined device.

12. The image information control apparatus according to claim 11, wherein the output-information generator generates the image as the output information by generating an image reflecting the image information and placing the generated image on an image portion within the second schematic image, the image portion being placed according to a relative position of the positional image within the first schematic image.

13. The image information control apparatus according to claim 11, wherein the first schematic image is a body mark that references the imaged portion of the ultrasound image.

14. The image information control apparatus according to claim 11, wherein the memory further memorizes association information that indicates a type of the image information to be superimposed onto the second schematic image for each of predetermined kinds of examinations using the ultrasound image; and
the output-information generator selects a certain one of the image information to be superimposed onto the second schematic image based upon the association information.

15. The image information control apparatus according to claim 11, wherein when the memory memorizes a plurality of the ultrasound images that have been taken from a same subject associated with a same one of the first schematic images, the output-information generator generates the image as the output information by superimposing images based on all of the positional images of the ultrasound images onto the second schematic image having the substantially same shape as the same first schematic image and further by superimposing each of the image information of the ultrasound images in vicinities of each of the images based on each of the positional images.

16. The image information control apparatus according to claim 11, wherein when the output-information generator generates a plurality of the image information of a same one of the ultrasound image, the output-information generator generates a plurality of the images as a plurality of the output information by superimposing each of the image information on the second schematic image based on a corresponding depth of each of the plurality of the image information of the ultrasound image.

17. The image information control apparatus according to claim 11, wherein the output-information generator generates the image as the output information only on a specified ultrasound image.

18. The image information control apparatus according to claim 11, further comprising a display, wherein when an operator specifies a particular one of the image information in the output information after reviewing the output information, the controller controls the display of the ultrasound image from which the specified one of the extracted image information is generated onto the display.

19. An image information control apparatus, comprising:
a memory configured to memorize position information indicating a position of a positional image on a first schematic image and a medical image, the first schematic image schematically representing an imaged portion of the ultrasound image, the positional image indicating a position of a region of the medical image, the positional image being set on the first schematic image by an operator user;
an output-information generator operationally connected to the memory and configured to generate an image information indicating a feature of the medical image memorized in the memory, generate an image by superimposing the image information on a second schematic image having the substantially same shape as the first schematic image based upon the position information memorized in the memory, and output the image to a predetermined device as output information; and a controller operationally connected to the output-information generator and configured to control an output of the output information to the predetermined device.

* * * * *